United States Patent [19]

Oswald

[11] 3,954,723

[45] May 4, 1976

[54] NOVEL POLYTHIOETHER DIOLS AND THEIR PREPARATION

[75] Inventor: Alexis A. Oswald, Mountainside, N.J.

[73] Assignee: Exxon Research & Engineering Co., Linden, N.J.

[22] Filed: Oct. 18, 1974

[21] Appl. No.: 516,088

Related U.S. Application Data

[60] Continuation-in-part of Ser. No. 326,108, Jan. 23, 1973, abandoned, which is a division of Ser. No. 47,109, June 17, 1970, Pat. No. 3,717,618, which is a continuation-in-part of Ser. No. 541,696, April 11, 1966, Pat. No. 3,592,798.

[52] U.S. Cl............................. 260/79; 204/159.22; 260/285.5 R; 260/31.8 Z; 260/37 R; 260/77.5 CR; 260/79.5 R; 260/79.5 C; 260/79.7; 260/609 R; 260/609 B
[51] Int. Cl.².................................. C08F 28/04
[58] Field of Search ............... 260/79, 609 R, 609 B

[56] References Cited
UNITED STATES PATENTS

| | | | |
|---|---|---|---|
| 2,916,519 | 12/1959 | Wegner et al.................... | 260/609 R |
| 3,592,798 | 7/1971 | Oswald .............................. | 260/887 |
| 3,625,925 | 12/1971 | Oswald et al. ..................... | 260/79 |
| 3,717,618 | 2/1973 | Oswald ............................... | 260/79 |

*Primary Examiner*—Melvyn I. Marquis
*Attorney, Agent, or Firm*—Joseph J. Allocca

[57] ABSTRACT

Terminally difunctional branched polythioether polyadducts are prepared by reacting dithiols with acetylenes under free radical conditions. Inherent to their method of preparation, the novel polythioethers contain the divalent carbon skeletons derived from their dithiol and acetylene monomer components in a regularly alternating manner. Dependent on the dithiol acetylene monomer ratio, the novel polymers contain thiol and/or vinyl sulfide end groups. Owing to their reactive, diterminal functions, they can be chain extended and crosslinked via known reactions to elastomers useful as mastics.

The polymers are crosslinked by various novel methods. For example, one mole of polythioether dithiol is reacted with two moles of an epoxide to produce the corresponding polythioether diol. The latter is then reacted with a diisocyanate to form a polythioether polyurethane of superior thermal and oxidative aging stability.

9 Claims, No Drawings

NOVEL POLYTHIOETHER DIOLS AND THEIR PREPARATION

CROSS REFERENCE TO RELATED APPLICATIONS

This application is a continuation-in-part of Ser. No. 326,108 filed Jan. 23, 1973, now abandoned, which is a division of Ser. No. 47,109, filed June 17, 1970 now U.S. Pat. No. 3,717,618, which in turn is a continuation-in-part of Ser. No. 541,696, filed Apr. 11, 1966, now U.S. Pat. No. 3,592,798.

BACKGROUND OF THE INVENTION

Polythioethers of high molecular weight are a widely investigated useful class of polymers. Most high molecular weight polythioethers have been prepared by the anionic polymerization of episulfides. With the exception of the highly crystalline polyethylene-sulfide, these polymers are useful as elastomers. These elastomers are generally copolymers. Minor amounts of olefinic unsaturation are incorporated into the polymer chain as crosslinking sites. This unsaturation is derived from an unsaturated episulfide comonomer.

The successful crosslinking of high molecular weight unsaturated episulfide copolymers initiated further research to find novel types of reactive polythioethers which can be crosslinked to rubbery networks. Such rubbers are of high interest mainly because their high sulfur content results in very good hydrocarbon solvent resistance and excellent aging characteristics.

The preparation of some terminally difunctional polythioethers by the addition of dithiols to diolefinic hydrocarbons has been known for some time. For example, Marvel and Chambers, J. Am. Chem. Soc. 70,999 (1948) and Marvel and Cripps, J. Polymer Sci. 8, 313 (1952) reported the reaction of dithiols with conjugated dienes such as butadiene and with dienes having isolated double bonds. However, such reactions proceeded at very slow rates and often resulted in unsaturated thioethers.

Numerous polythioethers were prepared by the ring opening of episulfides. The terminal groups of these polymers were generally not disclosed. However, they can be inferred on the basis of the initiators used since the mechanism of such ring opening reactions is known. It can be safely assumed that these polythioether preparations did not result in diterminally thiol and/or vinyl sulfide functional polymers. Inherent to the episulfide ring opening catalysts used, generally polythioethers containing only one thiol group were formed. The other end group derived from the initiator was usually a nonreactive hydrocarbon end group. For example, Boileau produced naphthyl terminated polythioether thiols by using sodium naphthyl as an initiator as described in the journal Compt. rend. (Paris) 254, 2774 (1962). Another example is given by the ethyl terminated polythioether thiol polymers which were produced by zinc diethyl initiator as disclosed in U.S. Pat. No. 3,222,326, incorporated herein by reference.

The use of amines as initiators of episulfide polymerization resulted in polyfunctional polythioethers. However, their use also resulted in the incorporation of nitrogen into the polymer (see, for example, U.S. Pat. No. 3,325,456).

Some polythioethers having reactive thiol end groups are disclosed in U.S. Pat. No. 3,337,487, incorporated herein by reference. These polythioethers result from the cleavage of nonfunctional very high molecular weight polymers derived by episulfide polymerization. Since episulfides such as ethylene and propylene episulfide cannot be copolymerized in an alternating manner, the method disclosed results in thiol terminated copolymers having a random structure.

PRIOR ART VERSUS THE PRESENT INVENTION

Polyethylene thioethers terminated by hydroxyl groups were described in U.S. Pat. 2,916,519 by C. Wegner et al, as being derived. e.g. from thiodiglycol, ethylene oxide, hydrogen sulfide and carbon disulfide.

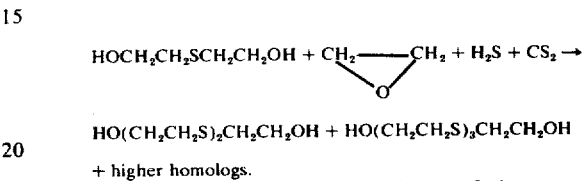

$HO(CH_2CH_2S)_2CH_2CH_2OH + HO(CH_2CH_2S)_3CH_2CH_2OH$

+ higher homologs.

These polymers in contrast to those of the present invention, have a high tendency to crystallize with increasing molecular weight. As such, they cannot be used as liquid prepolymers at room temperature.

In general, the previously known hydroxyl terminated polythioethers had nonbranched linear structures having a high crystallization tendency. In contrast, the present polythioether diols have pendant alkyl groups which inhibit their crystallization.

Nonbranched hydroxyl terminated polymers were also prepared via the dehydration of, e.g. thiodiglycol, as it is described in U.S. Patent 3,027,354 by H. Holtschmidt and E. Mueller:

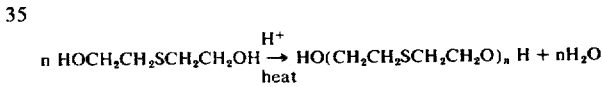

These prepolymers which contain oxy as well as thioether groups, were reacted with diisocyanates to produce polyurethane elastomers, as is also described in the same patent. The branched polythioethers of the present invention undergo a similar polyurethane formation when reacted with diisocycanates. However, the novel polyurethanes formed are free from the oxidative aging problems of polyurethanes containing oxyether groups.

Polythioether dithiols can be also reacted with diisocyanates to form polythiourethanes. These polymers, however, have a reduced thermal stability, due to the presence of the labile

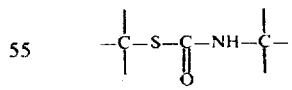

linkage. In contrast, the polyurethane derivatives of the present hydroxyl capped polythioethers are thermally stable because chain extension occurred via the formation of the stable

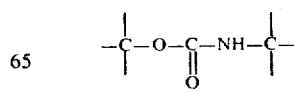

linkage.

SUMMARY OF THE INVENTION

Polythioethers, useful in the practice of this invention, are prepared by reacting an acetylenic compound with a dithiol. The polymers so formed are liquid or crystalline depending on the structure of the dithiol and acetylenic compound.

The polythioethers of this invention have the general formula:

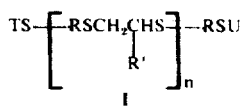

I wherein R is a $C_2$-$C_{30}$ divalent organic radical; R' is H or a $C_1$-$C_{30}$ hydrocarbyl radical, providing that either R has a branched structure or R' is alkyl; T and U are independently selected from the group consisting of H, -CH=CHR' and mixtures thereof and n varies from 1 to 1000.

The preferred terminally difunctional products of this invention are essentially colorless liquids or low melting solids having a number average molecular weight of about 200 to 200,000. They are readily crosslinked and chain extended by conventional methods.

Polymers of diterminal thiol functionality were found especially attractive for crosslinking. They could be converted by monoepoxides under anionic conditions via a surprisingly selective reaction to the corresponding polythioether diols as shown by the following scheme:

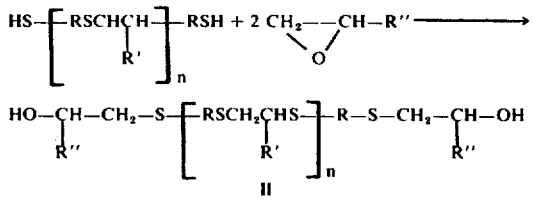

II wherein R'' is hydrogen, methyl, preferably hydrogen.

The polythioether diols in turn can be chain extended and crosslinked as indicated:

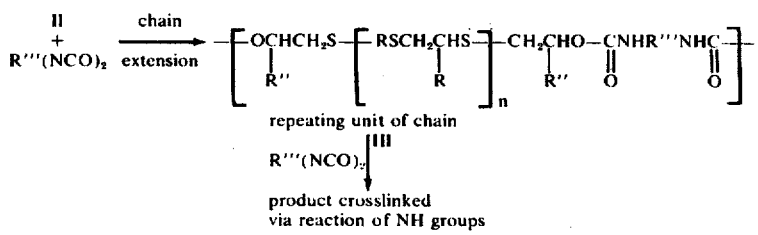

wherein R''' is phenylene, tolylene, xylylene, diphenylmethane, chlorophenylene, $C_2$ to $C_{16}$ polymethylene, such as hexamethylene, including polymethylene groups interrupted by thioether sulfur.

The crosslinked products are elastomers or resilient plastics having outstanding aging properties and solvent resistance.

DETAILED DESCRIPTION

Derivation of the Polymer Backbone

A method for preparing polythioethers having thiol or vinylic terminal functionality is described in copending U.S. application Ser. No. 541,696, now U.S. Pat. No. 3,592,798, incorporated herein by reference. The process involves the free radical addition of dithiols to acetylenic compounds. The structure of the resulting polythioether is dependent on the structure of the thiol and acetylenic compounds from which they are derived. Due to the nature of the reaction mechanism, the compounds so formed have incorporated therein the divalent carbon moiety derived from the acetylenic compound and the divalent alkylene bis-thio radical derived from the dithiol in a regular alternating manner.

Hence, the products of the reaction have a repeating structure which is broadly described by repeating unit of the general formula:

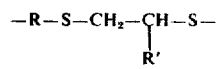

wherein the -S-R-S- fragment represents the residue derived from the thiol monomer and the

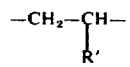

fragment is the residue of the acetylenic compound from which the polymer is prepared.

The dithiols suitable for use in the preparation of the intermediates of this invention have the general formula: HSRSH wherein R is a divalent organic radical. Preferably, R is a $C_2$-$C_{30}$ divalent organic radical.

The organic radical may have incorporated into its structure sulfur, oxygen or silicon in addition to carbon and hydrogen. The sulfur and oxygen containing organic radicals may contain thioether, ketone and carboxylic ester groups, but no oxyether group.

Both sulfur and oxygen in either of its forms may be present in the same organic radical.

In its preferred embodiment, the dithiol is a dithiol wherein R is a $C_2$ and $C_{30}$ divalent hydrocarbon radical. The divalent radical may be a saturated radical, e.g. alkylene, an unsaturated radical, e.g. acyclic or alicyclic alkenes or alkynes, a bis-alkylene substituted aromatic radical or an aromatic radical, e.g. m-phenylene.

The divalent alkylene radicals are preferably $C_2$-$C_{18}$ alkylene radicals, more preferably $C_2$-$C_{12}$ alkylene, most preferably $C_2$-$C_4$ alkylene, e.g. trimethylene. Illustrative examples of dithiols wherein R is a divalent alkylene radical are: decane dithiol, ethane dithiol, propane dithiol, butanedithiol, pentanedithiol, hexanedithiol, dodecane dithiol, docosanedithiol, triacontanedithiol, cyclohexane dithiol, cyclododecanedithiol, cyclohexane bis(ethanethiol), 2,2-dimethyl-1,3-propanedithiol, etc.

The acycylic or alicyclic alkene dithiols or alkyne dithiols suitable for use in the practice of this invention are internally unsaturated dithiols, preferably $C_4$-$C_{12}$ alkenedithiols, more preferably $C_4$-$C_8$ alkenedithiols. Illustrative examples of dithiols wherein R is an unsaturated divalent radical are 2-butene-1,4-dithiol, 3-hexene-1,6-dithiol, cyclohexene dithiol, 4-octene-1,8-dithiol, 2-butyne-1,4-dithiol, cyclododecene dithiol, 6-docosene-1,12-dithiol and 10-triacontene-1,30-dithiol.

Although the saturated and unsaturated thiols listed above are essentially terminally difunctional thiols, secondary dithiols are also suitable for use in the preparation of intermediates for the practice of this invention.

The aromatic compounds suitable for use as dithiol reactants are preferably $C_6$ to $C_{30}$ aromatic compounds; preferably these aromatic compounds contain about 6 to 10 carbon atoms, e.g. 8 carbon atoms. Illustrative examples of these aromatic compounds are m-phenylene dithiol, 1,5-naphthylene dithiol, biphenylene dithiol, terphenylene dithiol, quadriphenylene dithiol, xylene dithiol, durene dithiol and t-butylbenzene dithiol.

The $C_2$-$C_{30}$ divalent organic radicals containing sulfur, oxygen or silicon preferably contain 2 to 12 carbon atoms, more preferably about 4 to 10 carbon atoms, most preferably about 4 to 6 atoms. Illustrative examples of such organic dithiols suitable for use in the practice of this invention are thio-bis-ethanethiol, thio-bis-benzene-thiol, ethylene-bis-carboxyethanethiol, 3-hydroxy-propanedithiol, terephthaloyl-bis(methanethiol), dimethylsylyl-bis(ethanethiol) and diphenylsylyl-bis(ethanethiol).

Particularly preferred thiols are those compounds wherein R is a $C_2$-$C_4$ alkylene radical since such intermediates are especially reactive and yield polymers of outstanding resistance to autoxidation and hydrocarbon solvents.

The acetylenic compounds useful as starting materials have the general formula: $CH \equiv CR'$ wherein $R'$ is a hydrogen radical or a $C_1$-$C_{30}$ hydrocarbon radical. Preferably, $R'$ is (1) H; (2) a $C_1$-$C_{30}$ alkyl group, e.g. methyl, ethyl, etc.; (3) a $C_2$-$C_{20}$ alkenyl radical such as vinyl, allyl, etc.; (4) a $C_2$-$C_{30}$ alkynyl radical, e.g. ethynyl, and (5) a $C_7$-$C_{20}$ aralkyl radical such as benzyl, phenylethyl, naphthyl, methyl.

Where $R'$ is H, the compound is obviously acetylene. Preferably, $R'$ is a hydrocarbyl radical.

Where the hydrocarbyl radical is an alkyl group, it preferably comprises a $C_1$ to $C_{10}$ alkyl radical; more preferably $C_1$-$C_6$, most preferably $C_1$-$C_4$. $R'$ may be cycloalkyl. Illustrative examples of such alkyl radicals are methyl, propyl, hexyl, octyl, dodecyl, eicosyl, docosyl, triacontyl and cyclohexyl.

Where the hydrocarbyl radical is an alkenyl radical, it is preferably an internally unsaturated $C_4$-$C_{10}$ radical. Illustrative examples of such alkenyl radicals are 2-butenyl, 3-hexenyl, cyclohexenyl, 4-octenyl, cyclododecenyl, docosenyl, triacontenyl, etc.

The hydrocarbyl alkynyl radicals are preferably internally unsaturated radicals, more preferably $C_4$ to $C_6$ alkynyl radicals such as 3-hexynyl and triacontynyl.

Where $R'$ is an aralkyl, it is preferably a $C_7$ to $C_{10}$ aralkyl. Illustrative of aralkyl radicals are benzyl, phenylethyl, naphthylmethyl, phenyloctyl and phenyldocosyl.

Preferably, $R'$ is a hydrocarbyl radical of less than 10 carbon atoms. The preferred acetylenic compounds are those compounds in which $R'$ is a $C_1$ to $C_6$ hydrocarbyl radical, more preferably, a $C_1$-$C_4$ alkyl radical. The preferred acetylenic compounds are acetylene, methylacetylene, butylacetylene and benzylacetylene.

The reactions by which the products of this invention are prepared are represented by the following equations:

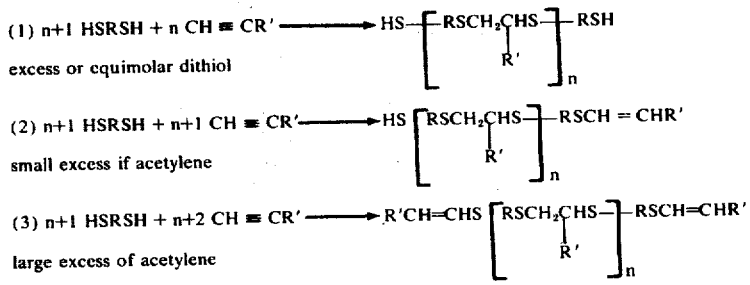

The preferred intermediates are essentially colorless liquid or low melting solids having a number average molecular weight of about 200 to 200,000, preferably about 500 to 20,000. Hence, "n" may vary from about 1 to about 1,000, preferably 2 to 1,000, more preferably "n" is about 2 to about 100, most preferably 3 to 40. The liquid polythioether products are particularly preferred in mastics and sealants. Such liquid adducts are essentially castable rubbers.

The liquid state of the polythioethers is strongly dependent on their structure. The tendency toward crystallinity is increased through the introduction of branching, e.g. $R' \neq H$ and selecting R so that it is branched and/or greater than a $C_2$ divalent carbon radical. It is well known that increasing the distance between subsequent sulfur atoms in a polythioether reduces crystallinity.

INTERMEDIATES AND PRODUCTS

The intermediates of this invention are broadly defined by the general formula:

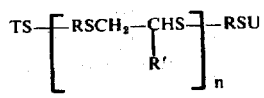

where R and $R'$ are as previously defined, T and U are independently selected from the group consisting of H and

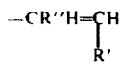

and n is about 1 to about 1,000. Preferably, R'' is H. Where at least one member of the group T and U is H, R must not be

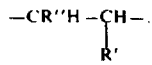

For example, where R'' is H and R' is methyl, R may not be

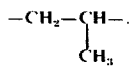

In a more specific embodiment of this invention, R is a divalent alkylene radical of the formula -C$_x$H$_{2x}$- and R' is -(C$_y$H$_{2y+1}$)- wherein x is 2 to 30, preferably 2 to 12, more preferably 2 to 4, e.g. 3; and y is 0 to 30, preferably 0 to 4. It is obvious that where y is 0 -(C$_y$H$_{2y+1}$)- is H, otherwise the formula denotes an alkyl radical.

In another specific embodiment, R is more simply —(CH$_2$)$_x$— and R' is —(C$_y$H$_{2y+1}$)— x and y being as previously defined.

The terminally difunctional polythioether compounds of this invention can be defined as thiol and/or vinyl sulfide terminated difunctional polythioether polyadducts. The preferred products are the dithiol terminated adducts.

The ratio of reactants present in the reaction zone has a strong effect upon the molecular weight of the final product. In general polymers having a number average molecular weight between 500 and 4000 are secured when an equal molar ratio of dithiol to acetylenic compound is present in the reaction zone. Higher molecular weight thiol terminated polythioethers are secured when the molar ratio of thiol compound to acetylenic compound is maintained between about 1:1.01 to 1:1.3.

Although the direct use of low molecular weight polythioether dithiols for the preparation of polymer articles is commercially less attractive, they can be advantageously used for the preparation of higher molecular weight polythioetherdithiols by reacting them with further amounts of an acetylene in the next step. For example:

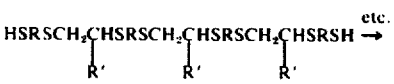

Preferred intermediate compositions include polythioetherdithiols of the formula:

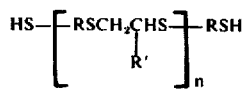

wherein R and R' are as previously defined and

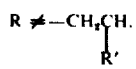

More preferably such polythioetherdithiols include those of the formula:

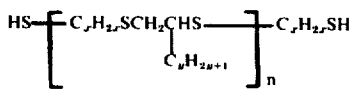

wherein x, y and n are as defined earlier and —C$_x$H$_{2x}$— does not equal —CH$_2$CH(C$_y$H$_{2y+1}$)—.

Further illustrative examples of polythioetherdithiols of this invention are:

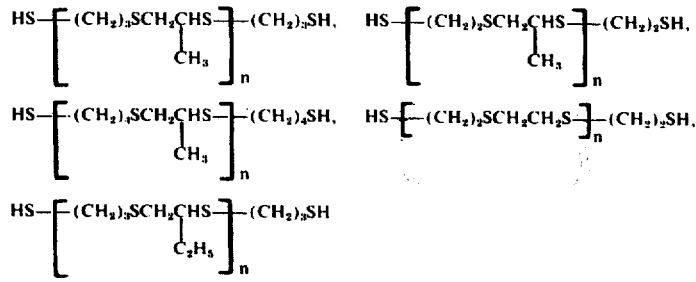

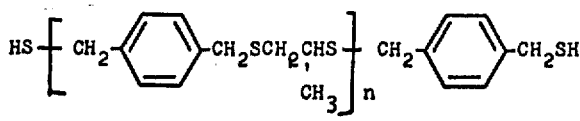

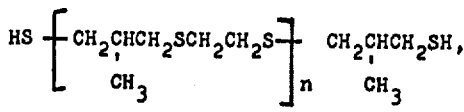

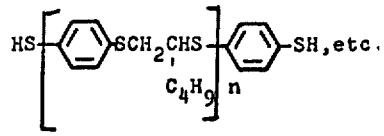

Another specific embodiment of the novel compositions includes diterminally functional polythioethers having one thiol and vinyl sulfide end group of the following formula:

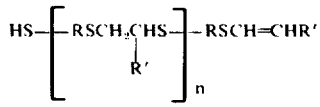

wherein R and R' are as previously defined with the limitation that

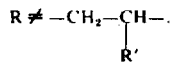

CHAIN EXTENSION AND CROSSLINKING

Although the addition products of the present invention have many uses as intermediates because of the thiol or vinyl terminal functionality present on the polymers, they find particular utility as the base substituent for mastic compositions. The thiol terminated addition products of this invention can be readily crosslinked to stable rubbery three-dimensional networks using a variety of techniques.

For example, the polythioetherdithiol addition products may be oxidatively chain extended by mixing the polymers with from 1 to 20 grams per 100 grams of polymer of dimethylsulfoxide and heating the total mixture at a temperature varying from 80 to 150°C. for a period ranging from 1 to 5 hours.

In another example, 5 parts of the polythioetherdithiol is mixed with 2 parts of a curing composition containing 50% of lead dioxide as an oxidizer, 5% stearic acid as a retarder and 45% dibutyl phthalate as a plasticizer. About 2.5 grams of carbon black of Thermax brand is also added as a filler. Dependent on the thiol functionality curing occurred in about 24 to 36 hours when the mixtures were allowed to stand at room temperature in a desiccator containing a saturated solution of aqueous sodium thiocyanate. Other metal peroxides, sulfur and organic peroxides can also be used for oxidative crosslinking.

For the oxidative crosslinking of polythioetherdithiols the addition of minor amounts of polythiols e.g. trithiols and tetrathiols is necessary. The oxidation of dithiols results in chain extension while the polythiols contribute to crosslinking as indicated by the following reaction scheme:

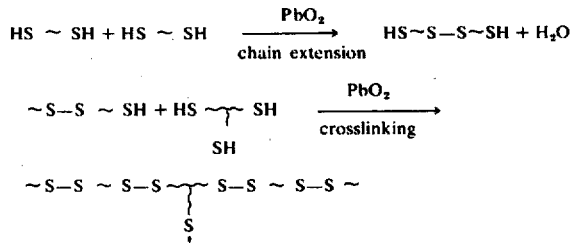

Dependent on the amount and functionality of the polythiol component vulcanized networks of various crosslink densities can be obtained. Suitable polythiols are 1,2,3-propanetrithiol, the trithiol adduct of $H_2S$ and trivinylcyclohexane, benzenetetrathiol, etc.

As another example of curing methods, polythioetherdithiols are treated with epoxides having at least 2 epoxide groups per molecule in the presence of a base catalyst usually an amine. For example, 1.2 mole equivalent of Epon-830, a bis-phenol-A-diglycydyl ether resin, is reacted with 1.0 mole equivalent of a polythioetherdithiol in the presence of 5 wt. % DMP-30 amine catalyst, i.e. tri-2,4,6-(dimethylaminomethyl)phenol. Chain extension takes place at room temperature due to the thiolepoxide reaction. The cure is completed in two hours at 100° due to the reaction of the hydroxy groups formed with the excess epoxide. The type of reactions involved are indicated by the following reaction scheme.

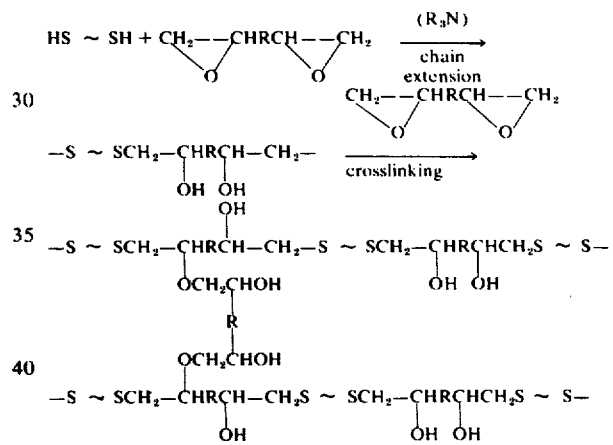

Polythioetherdithiols undergo similar amine catalyzed reactions with diepisulfides. These reactions, however, do not require heating for complete cures, since chain extension and crosslinking both occur under mild conditions.

Alternatively, the polythioetherdithiols can be cured with about equimolar amounts on an excess of a diisocyanate to produce polythiourethanes.

It was found in the present invention that it is particularly advantageous to modify the polythioetherdithiol with an equivalent amount of a monoepoxide at first and then crosslink the resulting polythioetherdiol with a diisocyanate. As is shown by the reaction scheme, such a reaction produces more stable polyurethanes rather than the less stable polythiourethanes.

In the reaction scheme, the formula of the polythioether dithiols is replaced by the symbol HS~SH. It is emphasized that the first reaction with the ethylene or propylene oxide is selective to produce hydroxyl terminated polymers substantially free from oxy-ether groups as shown:

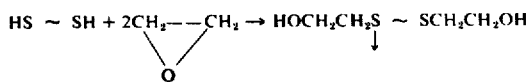

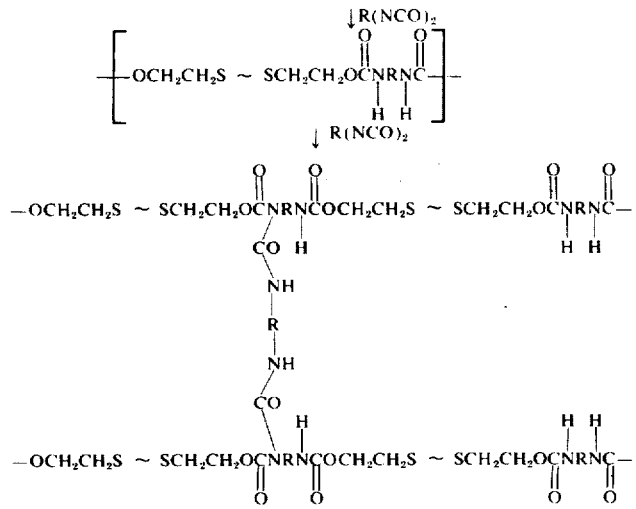

Such reactions can be also effectively and selectively catalyzed by $C_1$ to $C_4$ trialkyl amines such as triethylamine, trimethylamine. In the presence of the above catalysts, the opening of the epoxide ring by the thiol reactant occurs via an anionic mechanism. Accordingly, the use of a substituted epoxide such as propylene oxide results in disecondary diol products. Using the above catalysts, the formation of products containing oxy-ether groups is substantially avoided. This is due to the sharply reduced rate of the hydroxyl-epoxide reaction of the products compared to that of the thiol-epoxide reaction of the starting reactants.

The selective dithiol monoepoxide reactions are preferably carried out at temperatures between 10 and 100°C, more preferably, between 30° and 50°C. The preferred catalyst is triethylamine and the preferred epoxide is propylene oxide. It is preferred that the concentration of the amine be between 5 and 200, more preferably, 5 to 50 mole percent based on the dithiol. The amount of the epoxide reactant is preferably between 2 and 2.5 moles per dithiol.

The polythioether diol-diisocyanate reactions were carried out in the manner known for polyoxyether diol-diisocyanate reactions. Typical procedures are described in the monograph "Polyurethanes" which appeared as Volume XVI of the High Polymers Series. The latter was published by the Interscience Division of J. Wiley and Sons in New York, 1962.

Polythioetherdithiols can be also chain extended and crosslinked by reacting them with di- and polyolefinic and polyacetylenic unsaturates. It is preferable to use unsaturated compounds having olefinic bonds activated towards thiol addition. For chain extension diunsaturated compounds such as diacrylates, diacrylamides, dipropiolates, diallyl maleate, divinyl sulfone can be advantageously used, e.g.

linking reagents are triacrylates, triacrylamides, tripropiolates, tetraacrylamides. Crosslinking reactions with these reagents can be catalyzed with bases such as tertiary amines. such as polyolefins such as polyethylene, polypropylene, polyvinylchloride, ethylene-propylene copolymer, etc. Such blends can be advantageous because of their increased oxidation stability, particularly in the presence of phenolic inhibitors.

In such blends, the terminally vinyl and/or thiol functional polythioether is usually a minor component. It is preferable to use it in amounts less than 25 wt. %, more preferably between 0.05 and 10 wt. %.

Our terminally difunctional polymers can be also blended with asphalt and vulcanized thereafter. In such blends either the asphalt or the polythioether can be the major component although it is preferred to have major amounts of the asphalt.

Prior to curing operations, the addition products may be compounded with stabilizers, plasticizers or extender oils, asphalts an various types of fillers. For example, carbon black, petroleum, coke or mineral fillers may be incorporated into the polymer up to about 10 parts, preferably up to 200 parts, of filler per 100 parts of polymer. Among the carbon blacks that may be compounded with the addition product polymer are the channel blacks such as ETC, MPC, HPC, etc. (these letters denoting carbon black products well known to the trade), the furnace blacks including SRF, HAF, etc., and the thermal blacks. The mineral fillers which may be used include any of the usual noncarbon black fillers or pigments such as the oxides, hydroxides, sulfides, carbonates, and so forth of silicon, aluminum, magnesium, titanium, zinc or the like, or the silicates or aluminates of the various elements above-indicated.

The cured mastic compositions of this invention are highly resistant to ozone and oxygen degradation even

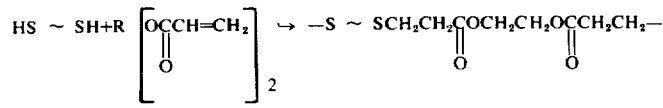

For crosslinking, tri- or polyfunctional unsaturated compounds can be used, alone or in addition to a diunsaturate. Examples of the types of such suitable crosslinking at elevated temperatures and are relatively immune to attack by organic solvents. Hence, the cured materials

13 find particular utility in automotive applications and as gasketing materials.

The invention will be further understood by reference to the following examples.

EXAMPLE 1

One gram mole (108 grams) of trimethylenedithiol was placed in a quartz pressure tube equipped with a magnetic stirrer. The tube was evacuated and 40 grams (1 gram mole) of methylacetylene was condensed therein. The reaction vessel was closed, placed in a water bath maintained at a temperature varying between 15° and 17°C., and the contents irradiated with constant stirring with a 70 watt high pressure Hanau immersion lamp. After a reaction period of 11 hours wherein the reactants were constantly agitated and subjected to ultraviolet irradiation, the reaction vessel was opened and the addition product recovered. All of the volatile starting materials and most of the volatile products were removed from the product by bubbling nitrogen for one hour through the product contained in a vessel maintained at a temperature of 150°C. and 25 millimeters of mercury. Following the distillation procedure, 134 grams (94% yield) of a polythioetherdithiol was obtained as clear, colorless, viscous liquid product.

Nuclear magnetic resonance analysis (NMR) of the product showed the presence of characteristic triplets centered at about 2.64 p.p.m. downfield fromm tetramethylsilane for the alpha-methylene, $SCH_2$, group; a characteristic quintriplet centered at about 1.74 p.p.m. for the middle methylene, $CH_2$, group; and a typical doublet at 1.34 p.p.m. for the methyl group. The lack of vinylic proton signals in the NMR spectrum indicated that the polythioether was saturated. The presence of the thiol groups was confirmed by potentiometric titration of the product with silver nitrate. The average molecular weight of the product as determined by low pressure osmometry in benzene solution was 1112.

On the basis of NMR analysis and molecular weight determination, the product is believed to have the following structure:

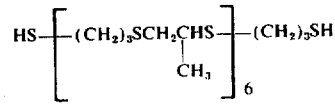

An elemental analysis of the product also supported the assumed structure. The calculated elemental composition for $HS[(CH_2)_3SCH_2CH(CH_3)S]_6(CH_2)_3SH$ (calculated molecular weight 1146): C, 47.15; H, 8.09; S, 44.76. Found: C, 47.70; H, 8.15; S, 44.91.

EXAMPLE 2

Following the procedure of Example 1, one gram mole (94 grams) of ethanedithiol was reacted with 40 grams (1 gram mole) of methylacetylene for 33.5 hours. After heating the crude product to 175°C. at 0.3 millimeters of mercury to remove the volatile reactants and products, 129 grams (96% yield) of viscous liquid polymeric product was recovered. The average molecular weight of the polymer as determined by low temperature osmometry in benzene solution was found to be 2532. From the molecular weight determination and an NMR structure analysis, the principal product was believed to have the following structural formula:

14

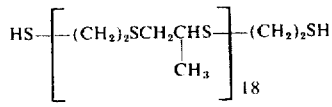

An elemental analysis of the product also supported the assumed structure. The calculated elemental composition for $C_{92}H_{186}S_{38}$ (molecular weight 2511; n = 18): C, 44.01; H, 7.46; S, 48.53. Found: C, 44.15; H, 7.52; S, 48.73.

EXAMPLE 3

Following the procedure of Example 1, 108 grams (1 gram mole) of 1,2-propane dithiol was reacted for 48 hours with 40 grams (1 gram mole) of methylacetylene. Following the reaction, the unreacted reagents and volatile adducts were removed by a one-hour distillation at 150°C. The final polythioetherdithiol product weighed 126 grams (85% yield). Its molecular weight was found to be 1604. The calculated composition for $C_{63}H_{128}S_{22}$ (molecular weight 1591): C, 47.56; H, 8.10; S, 44.34. Found: C, 47.36; H, 8.33; S, 43.79.

EXAMPLE 4

One-fifth molar quantities (21.6 grams each) of trimethylenedithiol were reacted with varying amounts of methylacetylene starting with an equal molar amount (8 grams) and with amounts in excess of equal molar quantities up to reactions where 100 mole % excess of methylacetylene was used. The reaction was conducted according to the procedure described in Example 1. The viscosities of the reacting mixtures increased with increasing excess of methylacetylene indicating the direct effect of the latter on the molecular weights of the polythioethers formed.

Molecular weight determinations of the various products indicated that an excess of 20 mole % of methylacetylene resulted in a product having a number average molecular weight of 4742. Products obtained when methylacetylene was present at 50 mole % and 100 % excess exhibited number average molecular weights of 4286 and 2532,respectively.

EXAMPLE 5

Three-tenths of a mole of trimethylenedithiol (32.4 grams) was reacted for 24 hours with a ten-fold molar excess of methylacetylene (120 grams, 3 gram moles) according to the procedure of Example 1. The resulting product was heated to 210°C. at 0.35 millimeters of mercury in a distillation apparatus to remove volatile materials. The residual product (30 grams, 86% yield) had a molecular weight of 842 as determined by low pressure osmometry. The NMR spectrum of the product showed that it had propenyl end groups as shown in the assumed product structure below.

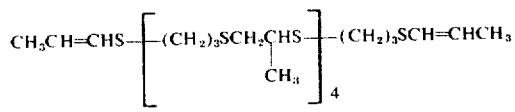

An NMR analysis of the distillate by-product (5 grams) showed that it consisted of a mixture of the following two monoadducts:

HS(CH₂)₃SCH=CHCH₃ and 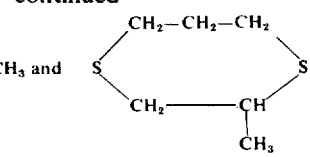

EXAMPLE 6

Into a quartz tube containing 94 grams (1 gram mole) of ethanedithiol was bubbled gaseous acetylene. The reactants were subjected to ultraviolet light irradiation and maintained at a temperature of 17°C. Acetylene addition was continued for 5 days. The resulting product was then heated to 115°C. at 0.3 millimeters of mercury pressure to remove unreacted dithiol. The residual product, weighing 20.5 grams was believed to be a diadduct of acetylene and ethanedithiol having the assumed structure:

HS(CH₂)₂S(CH₂)₂S(Ch₂)₂SH

The structure of the above product was confirmed by NMR analysis and thiol end group titration.

EXAMPLE 7

A mixture of 86.4 g. (0.20m) of trimethylenedithiol and 35 g. (0.875m) of methylacetylene contained in a Pyrex pressure tube was irradiated in an aluminum vessel from 7.5 cm distance by a Co⁶⁰ source emitting gamma-rays of about 6000 Curie intensity for 30 minutes. The tube was opened and evacuated to a pressure of 30 mm of mercury to remove the unreacted methyl acetylene. The crude product was then heated at 135°C. under 0.5 mm of mercury pressure to remove all the volatile components. This resulted in the recovery of 107 g. (about 90% yield) of the polyadduct in the form of a colorless, viscous liquid polymer. An NMR spectrum of the product indicated that it was virtually free from vinylic unsaturation. The product exhibited a number average molecular weight as determined by the osmotic method of 4330.

EXAMPLE 8

A mixture of 64.8 g. (0.6 m) of trimethylenedithiol and 48 g. (1.2m) of methylacetylene contained in a Pyrex pressure tube was irradiated as in the previous example with Co⁶⁰ plates for 30 minutes. Most of the excess methylacetylene was released on opening the reaction tube. The remaining unreacted material was removed on evacuation to 20 mm of mercury leaving 92.5 g. of residual product. On heating this product at 135°–138°C. under 0.15 mm of mercury pressure, 5.8 g. of a distillate was obtained. The residue consisted of 85 g. of a colorless somewhat viscous liquid. Its NMR spectrum showed the presence of vinylic unsaturation. Its average molecular weight as determined with the osmosis method was 1170.

EXAMPLE 9

A solution of 54 g. (0.5 m) of trimethylenedithiol and 20.3 g. (0.5075 m) of methylacetylene in 53 g. methyl sulfide contained in a quartz pressure tube was irradiated by ultraviolet light at 16°C. for 3.5 hours. The solvent was then removed at 30 mm of mercury pressure at room temperature. The remaining crude product (69 g.) was heated between 130°– 140°C. for 2 hours to remove the volatiles. The residual product (63 g.) was a colorless liquid of moderate viscosity having a number average molecular weight of 876.

EXAMPLE 10

A mixture of 54 g. (0.5 m) of trimethylenedithiol and 29.7 g. (0.55m) of ethylacetylene was irradiated at 16°C. with an ultraviolet lamp in the usual manner for 18 hours. The tube was opened and evacuated to a pressure of 30 mm of mercury resulting in the loss of 1.7 g. of unreacted ethylacetylene. The remaining crude product was heated at 140°C. under 0.2 mm for 2 hours to remove all the volatiles. The residual product obtained consisted of 73 g. (91%) of a colorless, viscous liquid. An NMR spectrum of the product indicated no vinylic unsaturation. An osmotic molecular weight determination of the product gave a value of 3943. The calculated molecular weight of the expected polythioetherdithiol having a degree of polymerization n, of 23 is 3916. Calculated elemental composition for C₁₆₇H₃₃₆S₄₉ (n = 23): C, 51.23; H, 8.64; S, 40.13. Found: C, 51.58; H, 8.50; S, 40.03.

EXAMPLE 11

A solution of 27 g. (1.6 m) of xylylene dimercaptan and 8.6 g. (0.215 m) of methylacetylene in 85 g. methyl sulfide, contained in a quartz pressure tube, was irradiated for 3.5 hours at 16°C. with ultraviolet light. The mixture was then washed with a 5% aqueous sodium hydroxide solution to remove the unreacted dimercaptan. The methyl sulfide phase was concentrated by distillation in vacuo and heated at 140°C. under 0.5 mm of mercury pressure. The residual polyadduct consisted of 5 g. of a viscous yellow-orange liquid. Its NMR spectrum showed a polyadduct backbone with no unsaturation. This suggested the expected polythioetherdithiol structure. The osmotic molecular weight of the product was found to be 875.

EXAMPLE 12

To a stirred melt. mixture of 34 g. (0.2 m) of p-xylylene dimercaptan and 8.2 g. (0.1 m) of 1-hexyne, 0.75 g. (0.0048 m) of azo-bis-isobutyronitrile was added at 70°C. The mixture was heated to 80°C. where an exothermic reaction was observed. After keeping the mixture at 80°C. for 6 hours, a sample of the resulting crude product was examined by NMR spectral analysis. The spectrum failed to show any unreacted hexyne nor any vinylic monoadduct intermediate present. The position and intensity of the observed NMR peaks agreed with those expected for the adduct having the structural formula:

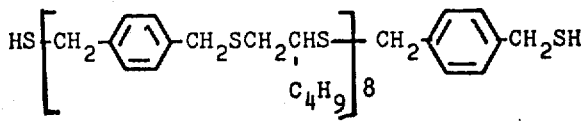

EXAMPLE 13

A mixture of 2.84 g. (0.02 m) of m-benzenedithiol and 1.64 g. (0.02 m) of hexyne was irradiated with ultraviolet light at 16°C. for 2.4 hours. The reaction mixture was sampled periodically for study by NMR. The hydrogen distribution of the samples indicated that 66% of the free thiol hydrogens disappeared during the first half hour of reaction. After 24 hours, the conversion was 80 % on the basis of thiol disappearance. An NMR spectrum also showed 2 vinylic protons for every thiol proton remaining. The rest of the spectrum supported the following assumed structure:

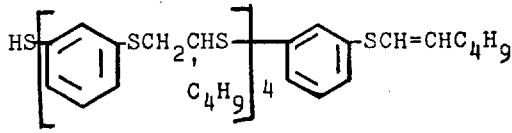

The calculated molecular weight for the above formula is 1122. The osmotic molecular weight determination gave a value of 1034. Calculated elemental composition for $C_{60}H_{80}S_{10}$ (n = 4): C, 64.24; H, 7.18; S, 25.58. Found: C, 64.36; H, 7.22; S, 28.94.

EXAMPLE 14

A stirred mixture of 30.5 g. (0.25 m) of tetramethylene dithiol and 14.2 g. (0.275 m) of 2-butylene was irradiated with ultraviolet light at 16°C. for 24 hours. The unconverted reactants and all other volatiles were then removed by distillation. After heating the residual product at 135°C. under 0.1 mm pressure for 2.5 hours, 31.5 g. (71.5% yield) of slightly yellow, somewhat viscous, clear liquid polymer was obtained. NMR supported the assumed structure of the polymer repeating unit and showed no vinylic unsaturation. A molecular weight determination by osmometry gave a value of 777. The calculated molecular weight of the assumed polythioetherdithiol product having 4 repeating units is 758. All the data together indicated that on the average, the following reaction took place;

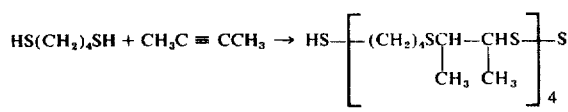

Calculated elemental composition for $C_{31}H_{64}S_{10}$ (n = 4): C, 49.16; H, 8.51; S, 42.33. Found: C, 48.97; H, 8.38; S, 42.74.

EXAMPLE 15

A mixture of 54 g. (0.5m) of trimethylenedithiol and 28.5 g. (0.525m) 2-butyne was allowed to stand at room temperature in a quartz pressure tube without any added catalyst. In a few minutes, the temperature of the mixture started to rise and in 10 minutes rose to about 60°C. The mixture then slowly came to ambient temperature and was left to stand for 160 hours. Subsequently, the unreacted starting materials and all other volatile compounds were removed. After 2½ hours at 135°C., under 0.2 mm mercury pressure, 57 g. (70%) of the residual polymer was obtained a clear, colorless, slightly viscous, liquid. An NMR spectrum of the polymer indicated the expected polythioetherdithiol structure. The molecular weight by the osmotic method was found to be 653. The calculated molecular weight for the assumed polythioetherdithiols having an average of 3 and 4 repeating units is 595 and 757, respectively. Consequently, our product can be best described by the following formula:

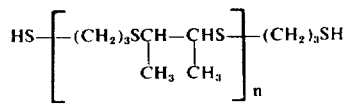

Calculated elemental composition for the polymer having n = 3, i.e., a summary formula $C_{24}H_{50}S_8$: C, 48.44; H, 8.46; S, 43.10. Calculated composition for the polymer having n = 1 i.e., $C_{31}H_{64}S_{10}$: C, 49.16; H, 8.51; S, 42.33. Found composition: C, 48.97; H, 8.38; S, 42.74. These data show that the average number of units, i.e., n for our product is between 3 and 4.

EXAMPLE 16

A polythioether dithiol of 1388 average molecular weight derived from trimethylene dithiol and methyl acetylene as described in Example 1 was used for the selective synthesis of the corresponding hydroxyethylated polythioethers via reaction with ethylene oxide.

Into 69.4 g (0.05 mole) of the stirred, previously nitrogenated liquid polythioether dithiol intermediate, 2.6 g. (0.05 mole) gaseous trimethyl amine catalyst was bubbled. Into the resulting mixture, 4.5 g (0.1 mole) gaseous ethylene oxide was introduced. The resulting reaction mixture was allowed to stand at ambient temperature for five days to complete the reaction. The trimethyl amine catalyst was subsequently removed in high vacuo to leave a colorless liquid residual polythioether diol product of the formula

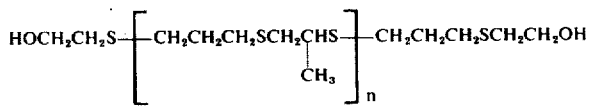

as indicated by nmr spectroscopy.

EXAMPLE 17

For a better characterization of polythioether dithiolepoxide reactions, a simple dithiol, ethane dithiol, was reacted with propylene oxide in the presence of triethylamine. As a result, low molecular weight products were obtained via the following anionic ring opening reactions:

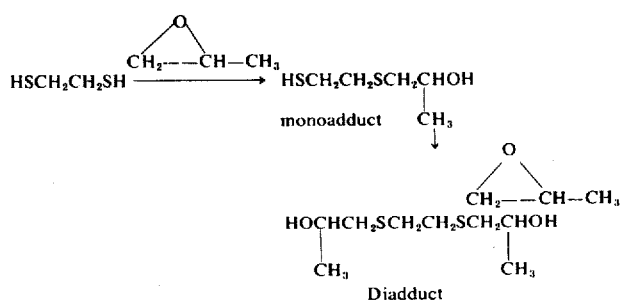

The products of these reactions could be readily analyzed by gas liquid chromatography (glc) and separated by fractional distillation in vacuo. Their structure could then be determined by nmr.

A series of experiments was run using 2.4 moles of the epoxide per mole dithiol on the 0.1 to 0.6 g mole dithiol scale. The catalyst was triethyl amine, usually 0.2 mole per mole dithiol. The epoxide was usually added dropwise to a stirred, ice-cooled mixture of the dithiol and the catalyst. Rapid exothermic reaction occurred after an induction period of several hours at room temperature. If the temperature runs out of control higher molecular weight oligomeric adduct by-products are also formed. Keeping the reaction temperature below 40° resulted in an essentially complete selectivity to the diadduct.

Equimolar amounts of the reactants provided both the mono and the diadducts.

In a large scale experiment, 561 g (6 mole) of ethane dithiol was reacted with 697 g (1.2 mole) of propylene oxide in the presence of 121 g (1.2 mole) triethyl amine at 40° to yield a crude diadduct of 90% purity according to glc.

On distillation of the crude product, 1107 g (88%) of the colorless liquid diadduct was obtained between 124°–130° at 0.1 mm. Nmr analysis of the product indicated the formation of a bis-secondary diol of the structure [CH$_2$SCH$_2$CH(CH$_3$)OH]$_2$.

Anal. Calcd. for C$_8$H$_{18}$O$_2$S$_2$: C, 45.68; H, 8.62; S, 30.49. Found: C, 45.80; H, 8.44; S, 30.72.

EXAMPLE 18

For a further characterization of the polythioether dithiol-epoxide reactions, trimethylene dithiol was reacted with ethylene oxide in the presence of triethyl amine.

A mixture of 27 g (0.25 mole) of 1,3-propanedithiol and 5.2 g (0.05 mole) of triethylamine was placed in a Pyrex pressure tube, equipped with a magnetic stirrer and a Teflon valve. Then, 32.5 g (0.74 mole) of ethylene oxide was condensed to the evacuated mixture at −70°C. The stirred reaction mixture was allowed to warm up in an ice bath and then kept in a room temperature bath overnight. Thereafter, the unreacted volatile epoxide was removed at 30 mm. A subsequent analysis of the reaction mixture by glc indicated that it contained the dithiol, the monoadduct and the diadduct in a 16:46:17 weight ratio.

What is claimed is:

1. A process for the selective preparation of polythioether diols comprising selectively reacting between 10° and 100°C. one mole of polythioether dithiol of the formula

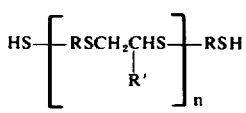

wherein n is about 2 to 1000, R is a divalent organic radical selected from the group consisting of C$_2$ to C$_{18}$ alkylene, C$_4$ to C$_{12}$ internally unsaturated alkene, C$_6$ to C$_{30}$ aromatic and C$_2$ to C$_{30}$ divalent organic radicals containing sulfur, oxygen or silicon, R' is selected from the group consisting of H, C$_1$-C$_{30}$ alkyl, C$_2$-C$_{30}$ alkenyl, C$_2$-C$_{30}$ alkynyl, C$_7$-C$_{20}$ aralkyl and mixtures thereof, except that R cannot equal —CH$_2$CH(R')—, with 2 moles of an epoxide of the formula

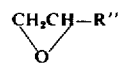

wherein R'' is hydrogen or methyl to obtain said polythioether diol of the formula

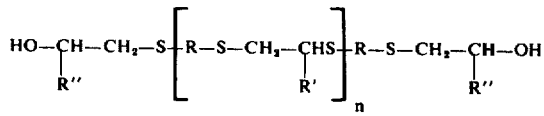

2. The process of claim 1 wherein the epoxide is propylene oxide.
3. The process of claim 1 wherein the reaction is catalyzed by a C$_1$ to C$_4$ trialkyl amine.
4. Polythioether diols of the formula

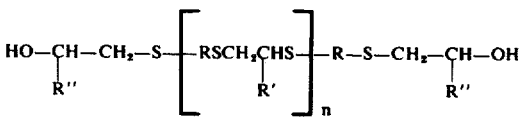

wherein n is 2 to 1000, R is a divalent organic radical selected from the group consisting of C$_2$ to C$_{18}$ alkylene, C$_4$ to C$_{12}$ internally unsaturated alkene, C$_6$ to C$_{30}$ aromatic and C$_2$ to C$_{30}$ divalent organic radicals containing sulfur, oxygen or silicon, R' is selected from the group consisting of H, C$_1$-C$_{30}$ alkyl, C$_2$-C$_{30}$ alkenyl, C$_2$-C$_{30}$ alkynyl, C$_7$-C$_{20}$ aralkyl and mixtures thereof except that R cannot equal -CH$_2$CH(R')- and R'' is H or methyl.
5. Polythioether diol of the formula

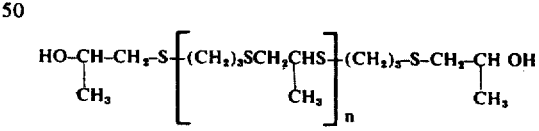

wherein n is 2 to 1000.

6. A process for the selective preparation of polythioether diols comprising selectively reacting between 10° and 100°C. one mole of a polythioether dithiol of the formula

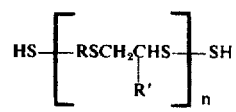

wherein n is about 2 to 1000, R is $C_2$ to $C_4$ alkylene radical, R' is a $C_1$ to $C_4$ alkyl radical except that R cannot eual $CH_2CH(R')$ with 2 moles of an epoxide of the formula

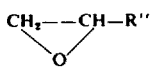

wherein R'' hydrogen or methyl to obtain said polythioether diol of the formula

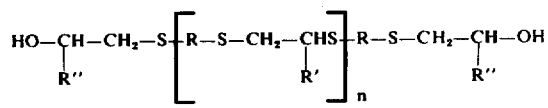

7. A process for the selective preparation of polythioether diols comprising selectively reacting between 10° and 100°C. one mole of a polythioether dithiol of the formula

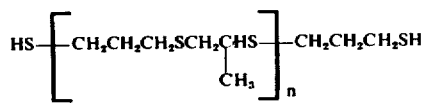

wherein n is about 2 to 1000 with 2 moles of ethylene oxide to obtain said polythioether diol of the formula

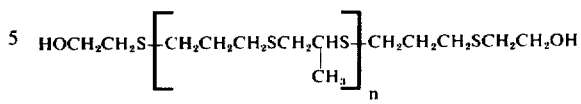

8. Polythioether diols of the formula

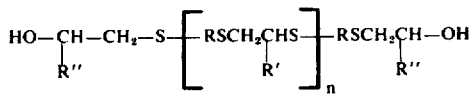

wherein n is 2 to 1000, R is a $C_2$ to $C_4$ alkylene radical, R' is a $C_1$ to $C_4$ alkyl radical R'' is hydrogen or methyl except that R cannot equal $CH_2CH(R')$.

9. A polythioether diol of the formula

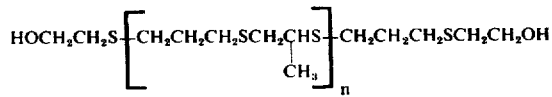

wherein n is 2 to 1000.

* * * * *